United States Patent
Ajemba et al.

(10) Patent No.: US 12,161,464 B2
(45) Date of Patent: Dec. 10, 2024

(54) MICRO MODELS AND LAYERED PREDICTION MODELS FOR ESTIMATING SENSOR GLUCOSE VALUES AND REDUCING SENSOR GLUCOSE SIGNAL BLANKING

(71) Applicant: MEDTRONIC MINIMED, INC., Northridge, CA (US)

(72) Inventors: Peter Ajemba, Canyon Country, CA (US); Keith Nogueira, Mission Hills, CA (US)

(73) Assignee: Medtronic MiniMed, Inc., Northridge (CA)

( * ) Notice: Subject to any disclaimer, the term of this patent is extended or adjusted under 35 U.S.C. 154(b) by 728 days.

(21) Appl. No.: 17/163,149

(22) Filed: Jan. 29, 2021

(65) Prior Publication Data

US 2022/0233109 A1     Jul. 28, 2022

Related U.S. Application Data

(63) Continuation of application No. 17/156,490, filed on Jan. 22, 2021.

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/7221* (2013.01); *A61B 5/7267* (2013.01);
(Continued)

(58) Field of Classification Search
CPC .............................. A61B 5/14532; G06N 20/20
See application file for complete search history.

(56) References Cited

U.S. PATENT DOCUMENTS

| 4,562,751 A | 1/1986 | Nason et al. |
| 4,573,994 A | 3/1986 | Fischell et al. |

(Continued)

FOREIGN PATENT DOCUMENTS

| CN | 103690240 B | 3/2016 |
| WO | 9736540 A1 | 10/1997 |
| WO | 2022159321 A2 | 7/2022 |

OTHER PUBLICATIONS

International Search Report and Written Opinion dated Aug. 11, 2022 in Application No. PCT/US2022/012243.
(Continued)

*Primary Examiner* — Daniel L Cerioni
(74) *Attorney, Agent, or Firm* — Weaver Austin Villeneuve & Sampson LLP

(57) ABSTRACT

Methods, systems, and devices for improving continuous glucose monitoring ("CGM") are described herein. More particularly, the methods, systems, and devices describe applying micro machine learning models to generate predicted sensor glucose values. The system may use the predicted sensor glucose values to display a sensor glucose value to a user. The layered models may generate more reliable sensor glucose predictions across many scenarios, leading to a reduction of sensor glucose signal blanking. The methods, systems, and devices described herein further comprise applying a plurality of micro model to estimate sensor glucose values under outlier conditions. The system may prioritize the models that are trained for certain outlier conditions when the system detects those outlier condition based on the sensor data.

18 Claims, 12 Drawing Sheets

(51) Int. Cl.
*G06N 20/00* (2019.01)
*G06N 20/20* (2019.01)
*G16H 40/63* (2018.01)
*G16H 50/20* (2018.01)
*G16H 50/30* (2018.01)

(52) U.S. Cl.
CPC ............ *A61B 5/7275* (2013.01); *A61B 5/742* (2013.01); *A61B 5/7475* (2013.01); *G06N 20/00* (2019.01); *G06N 20/20* (2019.01); *G16H 40/63* (2018.01); *G16H 50/20* (2018.01); *G16H 50/30* (2018.01)

(56) References Cited

U.S. PATENT DOCUMENTS

| | | |
|---|---|---|
| 4,678,408 A | 7/1987 | Nason et al. |
| 4,685,903 A | 8/1987 | Cable et al. |
| 4,755,173 A | 7/1988 | Konopka et al. |
| 5,391,250 A | 2/1995 | Cheney, II et al. |
| 5,482,473 A | 1/1996 | Lord et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Memoe et al. |
| 2010/0160463 A1 | 6/2010 | Causey, III et al. |
| 2017/0185733 A1 | 6/2017 | Nogueira et al. |
| 2018/0314975 A1* | 11/2018 | Zang ..................... G06N 20/20 |
| 2019/0175079 A1 | 6/2019 | Nishida et al. |
| 2020/0176121 A1* | 6/2020 | Dalal ..................... G16H 20/60 |
| 2020/0323437 A1 | 10/2020 | Lee et al. |
| 2020/0364596 A1 | 11/2020 | Zang et al. |
| 2020/0375549 A1 | 12/2020 | Wexler et al. |
| 2022/0233108 A1 | 7/2022 | Ajemba et al. |

OTHER PUBLICATIONS

U.S. Final Office Action dated Dec. 26, 2023 in U.S. Appl. No. 17/156,490 [MEDTP004US].

U.S. Non-Final Office Action dated Aug. 23, 2023, in U.S. Appl. No. 17/156,490 [MEDTP004US].

U.S. Non-Final Office Action dated May 3, 2023 in U.S. Appl. No. 17/156,490 [MEDTP004US].

Goodfellow, I., et al., Deep Learning, Chapter 1. Introduction, MIT Press, 2016, pp. 1-26 (available at https://www.deeplearningbook.org/contents/intro.html).

Food and Drug Administration, "Integrated continuous glucose monitoring system," 21 CFR 862.1355, 2008, 3 pages (available at https://www.ecfr.gov/current/title-21/chapter-I/subchapter-H/part-862/subpart-B/section-862.1355).

Um, T., "Awesome—Most Cited Deep Learning Papers," 2017, 13 pages (available at https://github.com/terryum/awesome-deep-learning-papers?tab=readme-ov-file#old-papers).

Lecun, Y., et al., "Deep Learning," Nature, 2015, vol. 521, pp. 436-444.

Lecun, Y., et al., "Gradient-Based Learning Applied to Document Recognition," Proceedings of the IEEE, Nov. 1998, vol. 86, No. 11, pp. 2278-2324.

* cited by examiner

100

150

MICRO MODELS AND LAYERED PREDICTION MODELS FOR ESTIMATING SENSOR GLUCOSE VALUES AND REDUCING SENSOR GLUCOSE SIGNAL BLANKING

RELATED APPLICATION DATA

This application claims the benefit of U.S. patent application Ser. No. 17/156,490, filed Jan. 22, 2021, entitled "MICRO MODELS AND LAYERED PREDICTION MODELS FOR ESTIMATING SENSOR GLUCOSE VALUES AND REDUCING SENSOR GLUCOSE SIGNAL BLANKING," which is incorporated herein by reference in its entirety.

FIELD

The present technology is generally related to sensor technology, including sensors used for sensing a variety of physiological parameters, e.g., glucose concentration.

BACKGROUND

Over the years, a variety of sensors have been developed for detecting and/or quantifying specific agents or compositions in a patient's blood, which enable patients and medical personnel to monitor physiological conditions within the patient's body. Illustratively, subjects may wish to monitor blood glucose levels in a subject's body on a continuing basis. Thus, glucose sensors have been developed for use in obtaining an indication of blood glucose levels in a diabetic patient. Such readings are useful in monitoring and/or adjusting a treatment regimen which typically includes the regular administration of insulin to the patient. Presently, a patient can measure his/her blood glucose ("BG") using a BG measurement device (i.e., glucose meter), such as a test strip meter, a continuous glucose measurement system (or a continuous glucose monitor), or a hospital BG test. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device.

SUMMARY

Conventional continuous glucose monitoring ("CGM") systems intermittently produce unreliable estimates of glucose concentration in a user's blood. Such an intermittent failure may have severe or even fatal effects on the user if they lead to neglecting or exacerbating hypoglycemia and hyperglycemia. For example, a lack of available or accurate sensor data may render a conventional CGM system ineffective and thus the estimated glucose readings produced by the conventional CGM system could be unreliable. This drawback is due to current systems' reliance on a single sensor glucose estimation model, which may be ill-equipped to handle problems that may occur. For example, sensor data may periodically become unavailable or limited, and conventional systems are unable to operate in such situations. To overcome these deficiencies, the methods and systems described herein train multiple models for accurately detecting glucose concentration during situations and/or detecting when a given situation arises. For example, a layered model approach, which includes models that are trained to predict sensor glucose values based on both sensor data and probabilistic information, may significantly reduce the frequency of blanking (e.g., removing, ignoring, or foregoing to transmit the sensor data to the sensor device or any other device with a display interface) by using a model (and a data type) specific for a given situation. For example, when sensor data is readily available, the system may use models that prioritize sensor data, while when sensor data is limited, the system may prioritize probabilistic information, generating pseudo-future estimates of sensor glucose values. Such a layered approach makes models available that are able to operate under a wide range of sensor conditions and allows the system to use a model best suited for a given situation. Methods and systems described herein therefore apply layered machine learning models to generate more reliable sensor glucose values.

Furthermore, the accuracy of this layered technique improves upon the ability of the CGM system to comply with government standards of sensor devices. Government agencies (e.g., the Federal Drug Administration ("FDA")) impose restrictions and requirements for the sensitivity and accuracy of CGMs. For example, CGM devices are required to meet numerous criteria (e.g., integrated continuous glucose monitoring ("iCGM") criteria) in order for the sensor data to be considered accurate. In order to comply with the iCGM criteria, the CGM system must ensure that sensor data which does not comply with the iCGM criteria is not shown to the user. With current systems, this leads to excessive blanking (e.g., removing, ignoring, or foregoing to transmit the sensor data to the sensor device or any other device with a display interface) in response to unreliable sensor data. Such excessive blanking may deprive a user of a sensor device of valuable sensor glucose data. Systems and methods described herein improve upon current systems by applying a layered machine learning model system to improve the reliability of sensor glucose measurements and thereby reduce blanking.

More particularly, methods, systems, and devices for continuous glucose monitoring are described. For example, the system may retrieve a plurality of machine learning models that are trained to predict sensor glucose values. In some embodiments, each machine learning model of the plurality of machine learning models may differ with respect to one or more data characteristics (e.g., sensor data availability, sensor data accuracy, probabilistic reliance, etc.). In some embodiments, the plurality of machine learning models may be trained using training data comprising clinical data on sensor glucose behavior. The system may receive CGM sensor data from a sensor device and input the sensor data into the plurality of machine learning models. In some embodiments, the system may receive outputs from the plurality of machine learning models indicating a plurality of predicted sensor glucose values. Finally, the system may generate for display, on a display interface, a sensor glucose value based on the plurality of predicted sensor glucose values. For example, the sensor glucose value may be based on a selection, average, weighted average, or any combination thereof of the plurality of predicted sensor glucose values.

Another limitation of conventional CGM systems is that they are ill-equipped to handle the wide range of conditions that sensor devices face. For example, users rely on receiving accurate sensor data under outlier conditions such as operating with a young user, a physically active user, a user with high glucose levels, a high elevation, high environmental temperatures, high sensor temperatures, high levels of wear by the user, an atypical location of wear on the body, manufacturing or fabrication variations, or other outlier conditions. Failure to produce accurate and reliable sensor glucose values under these outlier conditions can have severe or even fatal effects on a user of a sensor device. To overcome these deficiencies, the methods and systems described herein train a plurality of micro models for a single CGM system. The system trains each micro model to operate under a specific outlier condition, for example, using outlier training data specific to the outlier condition. However, certain outlier conditions are rare and thus insufficient clinical data exists for training a machine learning model to operate under those outlier conditions. Therefore, systems described herein train the models using a combination of outlier clinical data and standard training data for more robust training. When an outlier condition occurs, the system may identify the outlier condition based on a signature (e.g., trend, behavior, pattern) of input features of the sensor data. The system may then adjust the plurality of models to feature or prioritize certain models that are trained to operate under the identified outlier condition. Such an approach allows the CGM system to produce accurate sensor glucose values under a wide range of outlier conditions by adjusting the plurality of models to play to the strengths of specific models.

Furthermore, the accuracy of this technique improves upon the ability of the CGM system to comply with the FDA's iCGM criteria. Systems and methods described herein improve upon conventional systems by featuring different micro machine learning models under different outlier conditions in order to improve the accuracy of sensor glucose measurements and reduce blanking (e.g., due to data that does not comply with the iCGM criteria).

More particularly, methods, systems, and devices for continuous glucose monitoring are described. For example, the system may retrieve a plurality of machine learning models that are trained to predict sensor glucose values. In some embodiments, each machine learning model of the plurality of machine learning models may be trained for a particular outlier condition (e.g., using a combination of outlier clinical data and standard training data). The system may receive CGM sensor data from a sensor device and input the sensor data into the plurality of machine learning models. The system may identify a signature (e.g., trend, behavior, pattern) of input features in the sensor data. The system may then adjust the plurality of machine learning models to feature or prioritize one or more models associated with the identified signature of input features in the sensor data. The system may receive an output from the adjusted plurality of machine learning models indicating a predicted sensor glucose value. For example, the predicted sensor glucose value may be based on a selection, average, weighted average, maximum, minimum, median, or any combination thereof of the outputs of each micro model. In some embodiments, the system may display the predicted sensor glucose value to a user of a sensor device (e.g., via a display interface of the sensor device).

Various other aspects, features, and advantages will be apparent through the detailed description and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification "a portion," refers to a sub-part of, or the entirety of, a given item (e.g., data) unless the context clearly dictates otherwise.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A detailed description of embodiments of the invention will be made with reference to the accompanying drawings, wherein like numerals designate corresponding parts in the figures.

DETAILED DESCRIPTION

Figure 1:
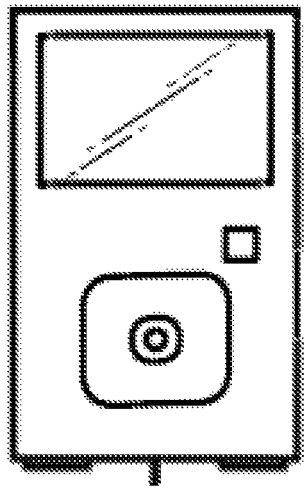
FIG. 1 illustrates wearable sensor electronics devices, in accordance with one or more embodiments.
Figure 1:
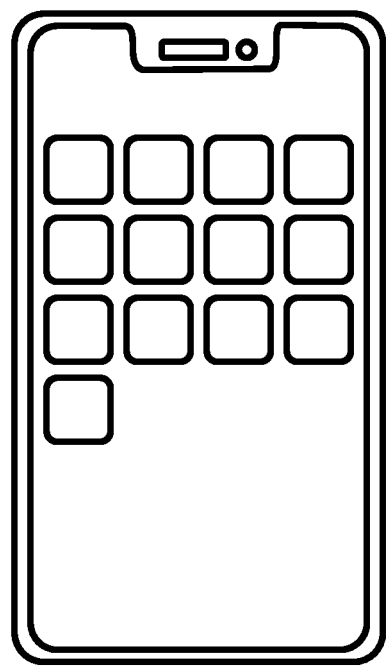

In the following description, reference is made to the accompanying drawings which form a part hereof and which illustrate several embodiments of the present inventions. It is understood that other embodiments may be utilized, and structural and operational changes may be made without departing from the scope of the present inventions.

The inventions herein are described below with reference to flowchart illustrations of methods, systems, devices, apparatus, and programming and computer program products. It will be understood that each block of the flowchart illustrations, and combinations of blocks in the flowchart illustrations, can be implemented by programing instructions, including computer program instructions (as can any menu screens described in the figures). These computer program instructions may be loaded onto a computer or other programmable data processing apparatus (such as a controller, microcontroller, or processor in a sensor electronics device) to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks, and/or menus presented herein. Programming instructions may also be stored in and/or implemented via electronic circuitry (e.g., storage circuitry, processing circuitry), including integrated circuits (ICs) and Application Specific Integrated Circuits (ASICs) used in conjunction with sensor devices, apparatuses, and systems. The following terms and definitions may also be used herein:

| Term | Definition |
| --- | --- |
| BG | Blood Glucose value in mg/dL typically from a fingerstick reading. Assumed use is for a sensor calibration |
| Calibrated Mode | Sensor operation mode in which the algorithm expects to receive BG calibrations as part of regular operation |
| CE | Calibration Error |
| CF (or calFactor) | Calibration Factor, sensor sensitivity to glucose used to calculate sensor glucose. Units are mg/dL/nA |
| CR (or cr) | Calibration Ratio, sensitivity based on a single BG and Isig |
| Discard | Packet flagged to be invalid based on Isig. |
| early calibration | Temporary CF update on the packet following a BG |
| EIS | Electrochemical Impedance Spectroscopy, Diagnostic capability to measure impedances at varying frequencies applied by the AFE IC |
| final calibration | Refers to updates to CF and other variables which may occur 10-15 minutes after a BG entry |
| fisig | Filtered Isig, used in calibration and SG calculation |
| GST | Glucose Sensor Transmitter |
| GOx | Glucose Oxidase |
| initialization | Sensor Initialization. This typically refers to data collection activities during sensor warm up period |
| Instant calibration error | CE check based on prior Isig, determines if a BG can be used for calibration |
| invalid packet | Refers to a packet being flagged as invalid. Packets flagged as invalid do not show SG to the user. |
| Isig | 5-minute reading of sensor current in nA. Sometimes called "raw Isig" |
| Isig1 | 1-minute reading of sensor current in nA. Sometimes called "1-minute Isig" |
| Isig Dip | Isig Dip Calibration. Refers to logic which may adjust CF following a calibration on an abnormally low Isig |
| MAX_CR | Maximum acceptable CR |
| MIN_CR | Minimum acceptable CR |
| Not Calibrated Mode | Sensor operation mode in which the algorithm does not expect to receive BG calibrations as part of regular operations. The algorithm can utilize BG calibrations if any is made available. |
| Packet (or SG Packet or Isig Packet) | Refers to the collection of variables calculated at the 5-minute interval, including Isig, sg, etc. |
| SG | Sensor Glucose value in mg/dL |
| Vset | Voltage potential |

FIG. 1 illustrates wearable sensor electronics devices 100 and 150, in accordance with one or more embodiments. In some embodiments, wearable sensor electronics device 100 may be an infusion pump. In some embodiments, the infusion pump may include a display. In some embodiments, wearable sensor electronics device 100 may be a combination infusion pump/glucose sensor. In some embodiments, wearable sensor electronics device 150 may be a cellular phone or any computing device. In some embodiments, wearable sensor electronics devices 100 and 150 may include a computer, a personal digital assistant, a pager, or any other suitable wearable device. In some embodiments, wearable sensor electronics devices 100 and 150 may house components described below in relation to FIGS. 2-6.

Figure 2:
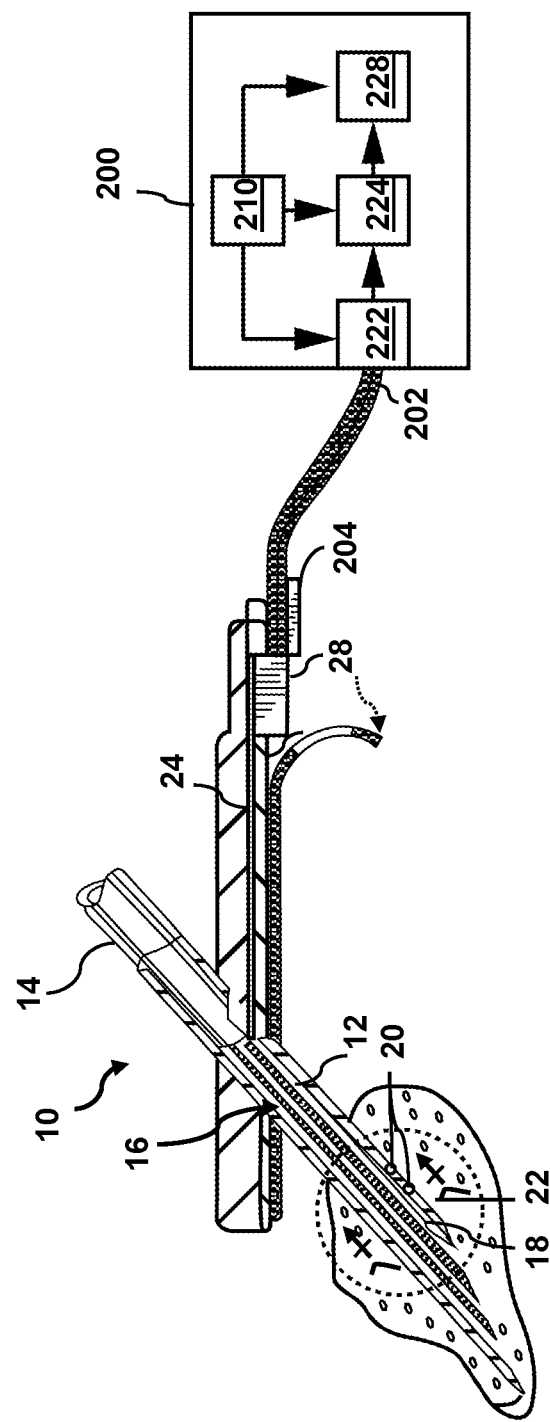
FIG. 2 is a perspective view of a subcutaneous sensor insertion set and block diagram of a sensor electronics device, in accordance with one or more embodiments.

FIG. 2 is a perspective view of a subcutaneous sensor insertion set and a block diagram of a sensor electronics device (e.g., wearable sensor electronics devices 100 or 150, as shown in FIG. 1, or any other suitable sensor electronics device). As illustrated in FIG. 2, a subcutaneous sensor set 10 is provided for subcutaneous placement of an active portion of a flexible sensor 12 (see, e.g., FIG. 3), or the like, at a selected site in the body of a user. The subcutaneous or percutaneous portion of the sensor set 10 includes a hollow, slotted insertion needle 14, and a cannula 16. The needle 14 is used to facilitate quick and easy subcutaneous placement of the cannula 16 at the subcutaneous insertion site. Inside the cannula 16 is a sensing portion 18 of the sensor 12 to expose one or more sensor electrodes 20 to the user's bodily fluids through a window 22 formed in the cannula 16. In one embodiment, the one or more sensor electrodes 20 may include a counter electrode, a reference electrode, and one or more working electrodes. After insertion, the insertion needle 14 is withdrawn to leave the cannula 16 with the sensing portion 18 and the sensor electrodes 20 in place at the selected insertion site.

In particular embodiments, the subcutaneous sensor set 10 facilitates accurate placement of a flexible thin film electrochemical sensor 12 of the type used for monitoring specific blood parameters representative of a user's condition. The sensor 12 monitors glucose levels in the body and may be used in conjunction with automated or semi-automated medication infusion pumps (e.g., wearable sensor electronics device 100, as shown in FIG. 1) of the external or implantable type to control delivery of insulin to a diabetic patient, as described, e.g., in U.S. Pat. Nos. 4,562,751; 4,678,408; 4,685,903 or 4,573,994, which are herein incorporated by reference.

Particular embodiments of the flexible electrochemical sensor 12 are constructed in accordance with thin film mask techniques to include elongated thin film conductors embedded or encased between layers of a selected insulative material such as polyimide film or sheet, and membranes. The sensor electrodes 20 at a tip end of the sensing portion 18 are exposed through one of the insulative layers for direct contact with patient blood or other body fluids, when the sensing portion 18 (or active portion) of the sensor 12 is subcutaneously placed at an insertion site. The sensing portion 18 is joined to a connection portion 24 that terminates in conductive contact pads, or the like, which are also exposed through one of the insulative layers. In alternative embodiments, other types of implantable sensors, such as chemical based, optical based, or the like, may be used.

As is known in the art, the connection portion 24 and the contact pads are generally adapted for a direct wired electrical connection to a suitable monitor or sensor electronics device 200 (e.g., wearable sensor electronics devices 100 or 150, as shown in FIG. 1, or any other suitable sensor electronics device) for monitoring a user's condition in response to signals derived from the sensor electrodes 20. Further description of flexible thin film sensors of this general type are to be found in U.S. Pat. No. 5,391,250, entitled METHOD OF FABRICATING THIN FILM SENSORS, which is herein incorporated by reference. The connection portion 24 may be conveniently connected electrically to the monitor or sensor electronics device 200 or by a connector block 28 (or the like) as shown and described in U.S. Pat. No. 5,482,473, entitled FLEX CIRCUIT CONNECTOR, which is also herein incorporated by reference. Thus, in accordance with some embodiments, subcutaneous sensor sets 10 may be configured or formed to work with either a wired or a wireless characteristic monitor system.

The sensor electrodes 20 may be used in a variety of sensing applications and may be configured in a variety of ways. For example, the sensor electrodes 20 may be used in physiological parameter sensing applications in which some type of biomolecule is used as a catalytic agent. For example, the sensor electrodes 20 may be used in a glucose and oxygen sensor having a glucose oxidase (GOx) enzyme catalyzing a reaction with the sensor electrodes 20. The sensor electrodes 20, along with a biomolecule or some other catalytic agent, may be placed in a human body in a vascular or non-vascular environment. For example, the sensor electrodes 20 and biomolecule may be placed in a vein and be subjected to a blood stream or may be placed in a subcutaneous or peritoneal region of the human body.

The monitor 200 may also be referred to as a sensor electronics device 200. The monitor 200 may include a power source 210, a sensor interface 222, processing electronics 224, and data formatting electronics 228. The monitor 200 may be coupled to the sensor set 10 by a cable 202 through a connector that is electrically coupled to the connector block 28 of the connection portion 24. In an alternative embodiment, the cable may be omitted. In this embodiment, the monitor 200 may include an appropriate connector for direct connection to the connection portion 204 of the sensor set 10. The sensor set 10 may be modified to have the connector portion 204 positioned at a different location, e.g., on top of the sensor set to facilitate placement of the monitor 200 over the sensor set.

In one embodiment, the sensor interface 222, the processing electronics 224, and the data formatting electronics 228 are formed as separate semiconductor chips, however, alternative embodiments may combine the various semiconductor chips into a single, or multiple customized semiconductor chips. The sensor interface 222 connects with the cable 202 that is connected with the sensor set 10.

The power source 210 may be a battery. The battery can include three series silver oxide 357 battery cells. In alternative embodiments, different battery chemistries may be utilized, such as lithium-based chemistries, alkaline batteries, nickel metal hydride, or the like, and a different number of batteries may be used. The monitor 200 provides power to the sensor set via the power source 210, through the cable 202 and cable connector 204. In one embodiment, the power is a voltage provided to the sensor set 10. In another embodiment, the power is a current provided to the sensor set 10. In an embodiment, the power is a voltage provided at a specific voltage to the sensor set 10.

Figure 3:
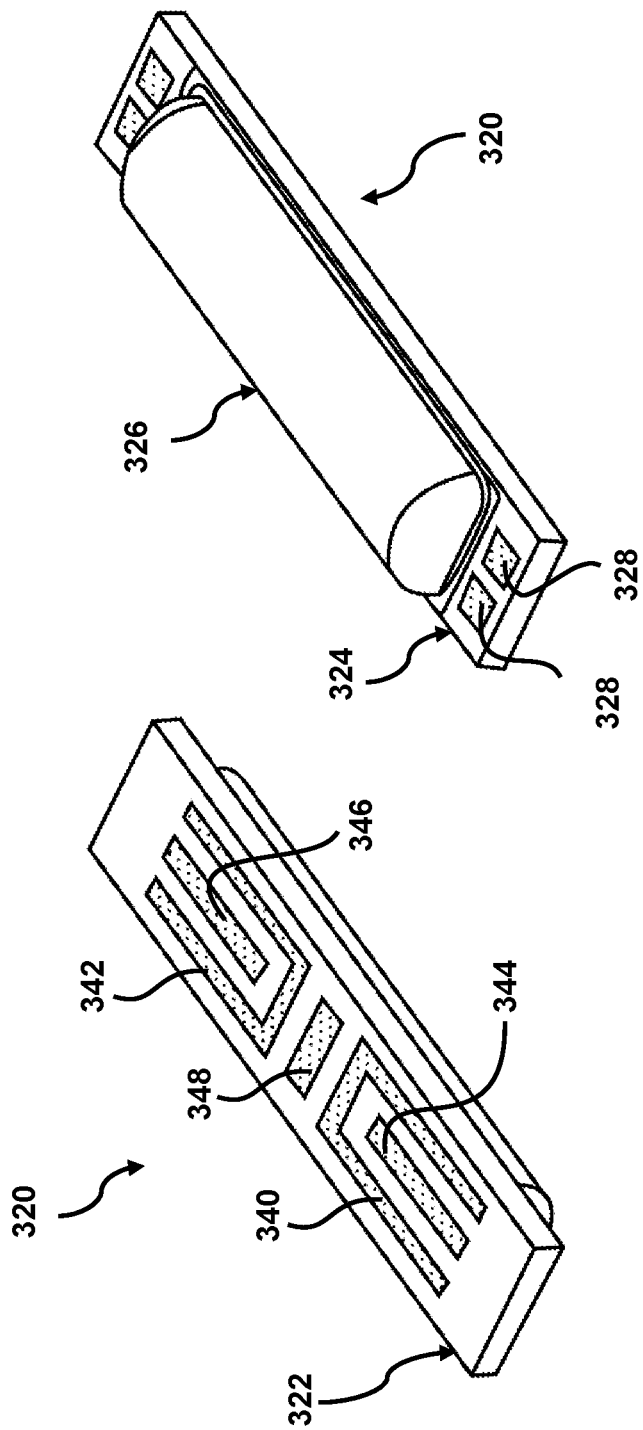
FIG. 3 illustrates a substrate having two sides, a first side which contains an electrode configuration and a second side which contains electronic circuitry, in accordance with one or more embodiments.

FIG. 3 illustrates an implantable sensor, and electronics for driving the implantable sensor in accordance with one embodiment. FIG. 3 shows a substrate 320 having two sides, a first side 322 of which contains an electrode configuration and a second side 324 of which contains electronic circuitry (e.g., storage circuitry, processing circuitry, etc.). As may be seen in FIG. 3, a first side 322 of the substrate comprises two counter electrode-working electrode pairs 340, 342, 344, 346 on opposite sides of a reference electrode 348. A second side 324 of the substrate comprises electronic circuitry. As shown, the electronic circuitry may be enclosed in a hermetically sealed casing 326, providing a protective housing for the electronic circuitry. This allows the sensor substrate 320 to be inserted into a vascular environment or other environment which may subject the electronic circuitry to fluids. By sealing the electronic circuitry in a hermetically sealed casing 326, the electronic circuitry may operate without risk of short circuiting by the surrounding fluids. Also shown in FIG. 3 are pads 328 to which the input and output lines of the electronic circuitry may be connected. The electronic circuitry itself may be fabricated in a variety of ways. According to an embodiment, the electronic circuitry may be fabricated as an integrated circuit using techniques common in the industry.

Figure 4:
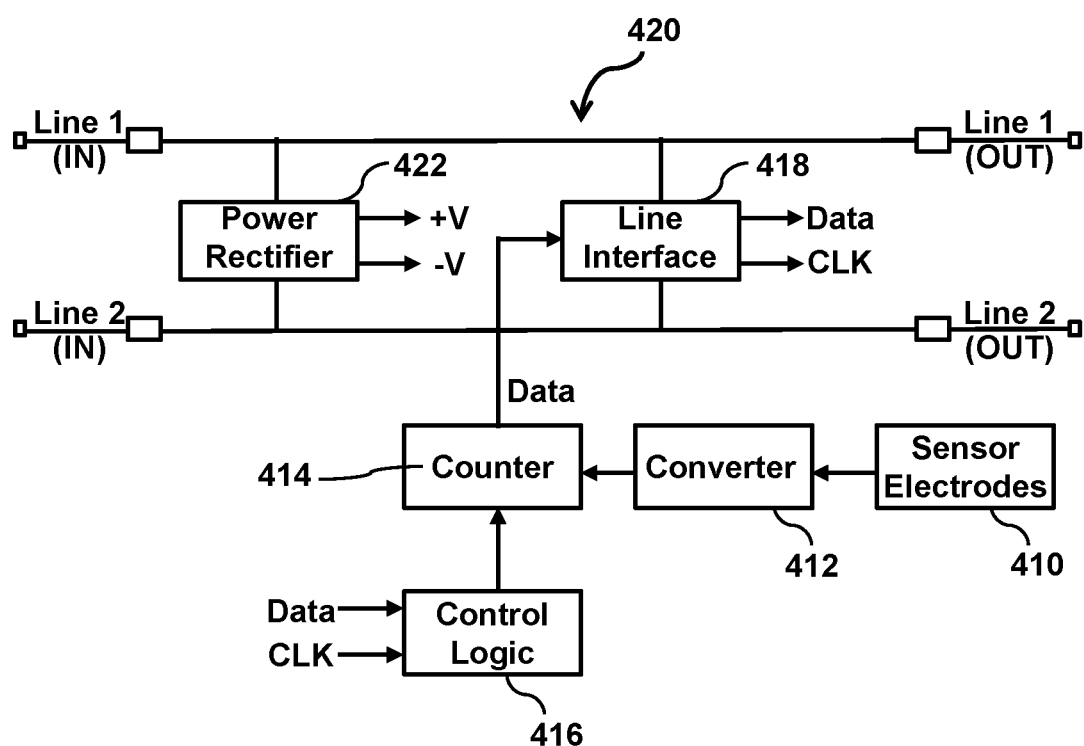
FIG. 4 illustrates a block diagram of a sensor electronics device and a sensor including a plurality of electrodes, in accordance with one or more embodiments.

FIG. 4 illustrates a general block diagram of an electronic circuit for sensing an output of a sensor according to one embodiment. At least one pair of sensor electrodes 410 may interface to a data converter 412, the output of which may interface to a counter 414. The counter 414 may be controlled by control logic 416. The output of the counter 414 may connect to a line interface 418. The line interface 418 may be connected to input and output lines 420 and may also connect to the control logic 416. The input and output lines 420 may also be connected to a power rectifier 422.

The sensor electrodes 410 may be used in a variety of sensing applications and may be configured in a variety of ways. For example, the sensor electrodes 410 may be used in physiological parameter sensing applications in which some type of biomolecule is used as a catalytic agent. For example, the sensor electrodes 410 may be used in a glucose and oxygen sensor having a GOx enzyme catalyzing a reaction with the sensor electrodes 410. The sensor electrodes 410, along with a biomolecule or some other catalytic agent, may be placed in a human body in a vascular or non-vascular environment. For example, the sensor electrodes 410 and biomolecule may be placed in a vein and be subjected to a blood stream.

Figure 5:
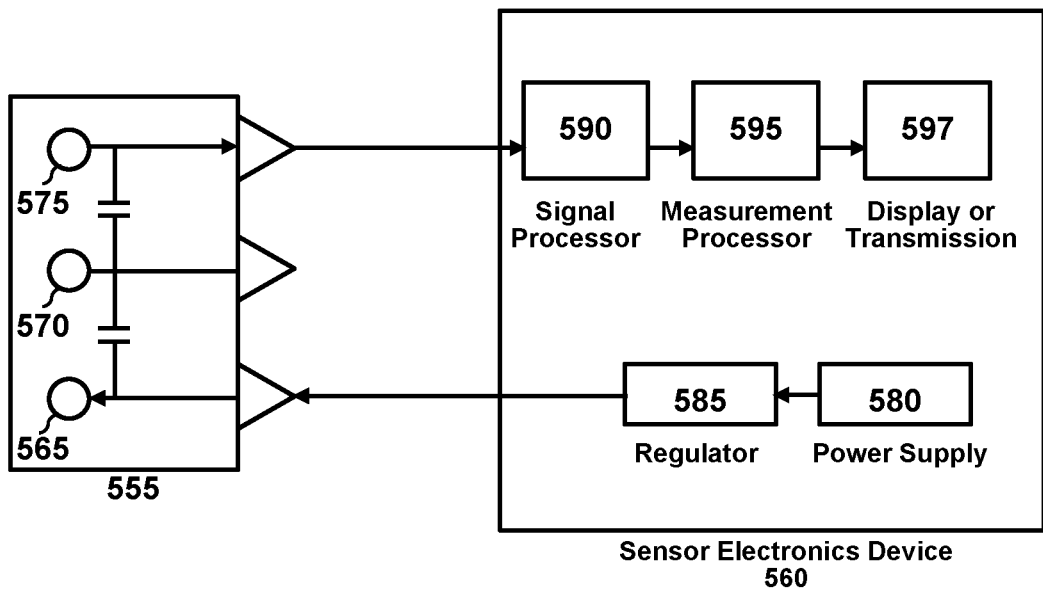
FIG. 5 illustrates an alternative embodiment of the invention including a sensor and a sensor electronics device, in accordance with one or more embodiments.
Figure 5:
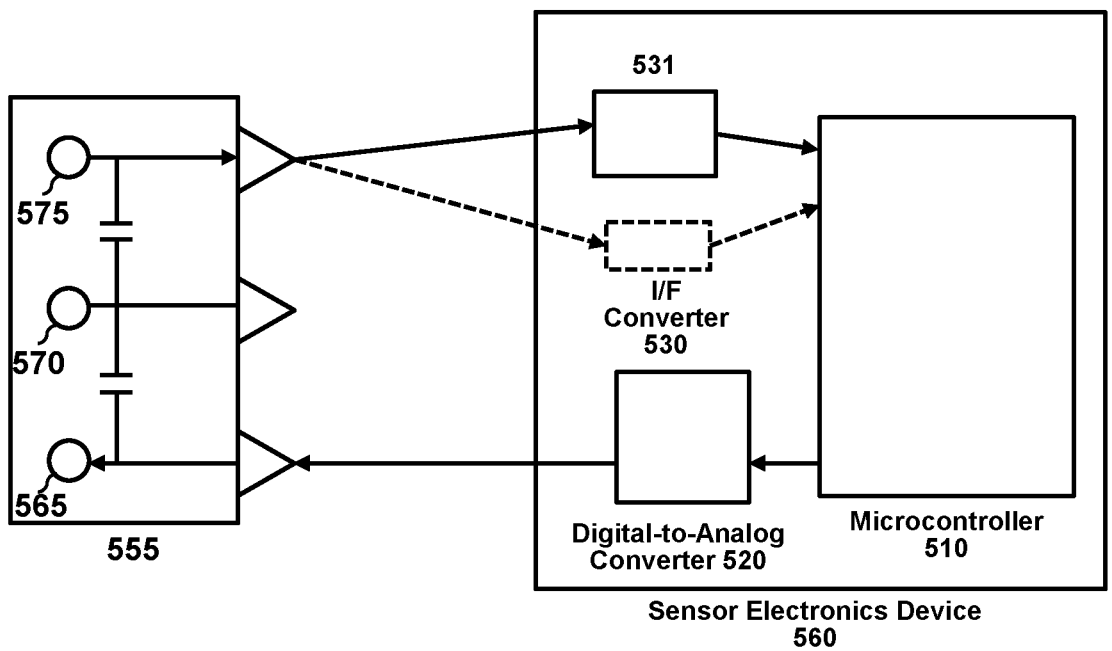

FIG. 5 illustrates a block diagram of a sensor electronics device (e.g., wearable sensor electronics devices 100 or 150, as shown in FIG. 1, or any other suitable sensor electronics device) and a sensor including a plurality of electrodes according to an embodiment herein. FIG. 5 includes system 500. System 500 includes a sensor 555 and a sensor electronics device 560. The sensor 555 includes a counter electrode 565, a reference electrode 570, and a working electrode 575. The sensor electronics device 560 includes a power supply 580, a regulator 585, a signal processor 590, a measurement processor 595, and a display/transmission module 597. The power supply 580 provides power (in the form of either a voltage, a current, or a voltage including a current) to the regulator 585. The regulator 585 transmits a regulated voltage to the sensor 555. In one embodiment, the regulator 585 transmits a voltage to the counter electrode 565 of the sensor 555.

The sensor 555 creates a sensor signal indicative of a concentration of a physiological characteristic being measured. For example, the sensor signal may be indicative of a blood glucose reading. In an embodiment utilizing subcutaneous sensors, the sensor signal may represent a level of hydrogen peroxide in a subject. In an embodiment where blood or cranial sensors are utilized, the amount of oxygen is being measured by the sensor and is represented by the sensor signal. In an embodiment utilizing implantable or long-term sensors, the sensor signal may represent a level of oxygen in the subject. The sensor signal is measured at the working electrode 575. In one embodiment, the sensor signal may be a current measured at the working electrode. In an embodiment, the sensor signal may be a voltage measured at the working electrode.

The signal processor 590 receives the sensor signal (e.g., a measured current or voltage) after the sensor signal is measured at the sensor 555 (e.g., the working electrode). The signal processor 590 processes the sensor signal and generates a processed sensor signal. The measurement processor 595 receives the processed sensor signal and calibrates the processed sensor signal utilizing reference values. In one embodiment, the reference values are stored in a reference memory and provided to the measurement processor 595. The measurement processor 595 generates sensor measurements. The sensor measurements may be stored in a measurement memory (not shown) or by circuitry (e.g., storage circuitry). The sensor measurements may be sent to a display/transmission device to be either displayed on a display in a housing with the sensor electronics or transmitted to an external device.

The sensor electronics device 560 may be a monitor which includes a display to display physiological characteristics readings. The sensor electronics device 560 may also be installed in a desktop computer, a pager, a television including communications capabilities, a laptop computer, a server, a network computer, a personal digital assistant (PDA), a portable telephone including computer functions, an infusion pump including a display (e.g., wearable sensor electronics device 100, as shown in FIG. 1), a glucose sensor including a display, and/or a combination infusion pump/glucose sensor (e.g., wearable sensor electronics device 100, as shown in FIG. 1). The sensor electronics device 560 may be housed in a blackberry (e.g., wearable sensor electronics device 150, as shown in FIG. 1), a network device, a home network device, or an appliance connected to a home network.

FIG. 5 also includes system 550. System 550 includes a sensor electronics device 560 and a sensor 555. The sensor includes a counter electrode 565, a reference electrode 570, and a working electrode 575. The sensor electronics device 560 includes a microcontroller 510 and a digital-to-analog converter (DAC) 520. The sensor electronics device 560 may also include a current-to-frequency converter (I/F converter) 530.

The microcontroller 510 includes software program code, which when executed, or programmable logic which, causes the microcontroller 510 to transmit a signal to the DAC 520, where the signal is representative of a voltage level or value that is to be applied to the sensor 555. The DAC 520 receives the signal and generates the voltage value at the level instructed by the microcontroller 510. In one embodiment, the microcontroller 510 may change the representation of the voltage level in the signal frequently or infrequently. Illustratively, the signal from the microcontroller 510 may instruct the DAC 520 to apply a first voltage value for one second and a second voltage value for two seconds.

The sensor 555 may receive the voltage level or value. In one embodiment, the counter electrode 565 may receive the output of an operational amplifier which has as inputs the reference voltage and the voltage value from the DAC 520. The application of the voltage level causes the sensor 555 to create a sensor signal indicative of a concentration of a physiological characteristic being measured. In an embodiment, the microcontroller 510 may measure the sensor signal (e.g., a current value) from the working electrode. Illustratively, a sensor signal measurement circuit 531 may measure the sensor signal. In an embodiment, the sensor signal measurement circuit 531 may include a resistor and the current may be passed through the resistor to measure the value of the sensor signal. In an embodiment, the sensor signal may be a current level signal and the sensor signal measurement circuit 531 may be a current-to-frequency (I/F) converter 530. The current-to-frequency converter 530 may measure the sensor signal in terms of a current reading, convert it to a frequency-based sensor signal, and transmit the frequency-based sensor signal to the microcontroller 510. In some embodiments, the microcontroller 510 may be able to receive frequency-based sensor signals easier than non-frequency-based sensor signals. The microcontroller 510 receives the sensor signal, whether frequency-based or non-frequency-based, and determines a value for the physiological characteristic of a subject, such as a blood glucose level. The microcontroller 510 may include program code, which when executed or run, is able to receive the sensor signal and convert the sensor signal to a physiological characteristic value. In one embodiment, the microcontroller 510 may convert the sensor signal to a blood glucose level. In an embodiment, the microcontroller 510 may utilize measurements stored within an internal memory or by circuitry (e.g., storage circuitry) in order to determine the blood glucose level of the subject. In an embodiment, the microcontroller 510 may utilize measurements stored within a memory external to the microcontroller 510 or by circuitry to assist in determining the blood glucose level of the subject.

After the physiological characteristic value is determined by the microcontroller 510, the microcontroller 510 may store measurements of the physiological characteristic values for a number of time periods. For example, a blood glucose value may be sent to the microcontroller 510 from the sensor in intervals (e.g., every second or five seconds), and the microcontroller may save sensor measurements in intervals (e.g., for five minutes or ten minutes of BG readings). The microcontroller 510 may transfer the measurements of the physiological characteristic values to a display on the sensor electronics device 560. For example, the sensor electronics device 560 may be a monitor which includes a display that provides a blood glucose reading for a subject. In one embodiment, the microcontroller 510 may transfer the measurements of the physiological characteristic values to an output interface of the microcontroller 510. The output interface of the microcontroller 510 may transfer the measurements of the physiological characteristic values, e.g., blood glucose values, to an external device, e.g., an infusion pump (e.g., wearable sensor electronics device 100, as shown in FIG. 1), a combined infusion pump/glucose meter (e.g., wearable sensor electronics device 100, as shown in FIG. 1), a computer, a personal digital assistant, a pager, a network appliance, a server, a cellular phone (e.g., wearable sensor electronics device 150, as shown in FIG. 1), or any computing device.

Figure 6:
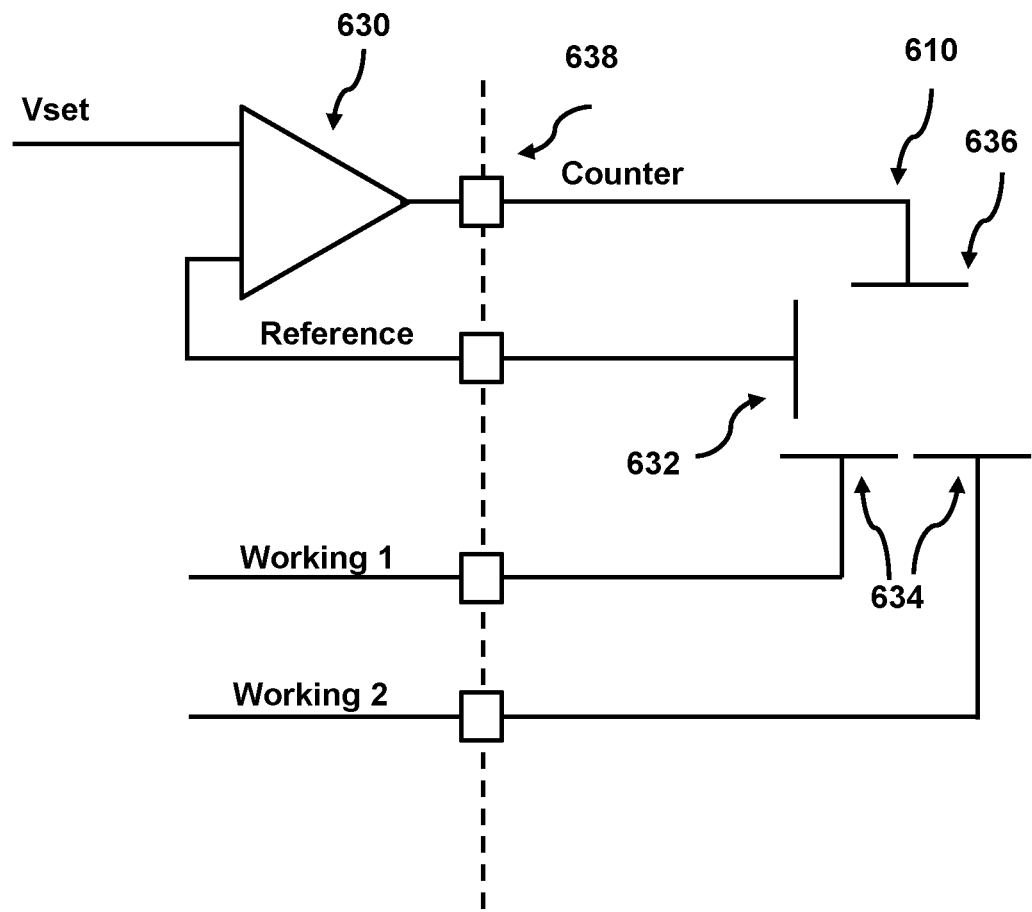
FIG. 6 illustrates an electronic block diagram of the sensor electrodes and a voltage being applied to the sensor electrodes, in accordance with one or more embodiments.

FIG. 6 illustrates an electronic block diagram of the sensor electrodes and a voltage being applied to the sensor electrodes according to an embodiment. In some embodiments, FIG. 6 may illustrate an electrode with a GOx sensor and/or an electrode capable of sensing GOx. For example, FIG. 6 may illustrate a working electrode with a GOx sensor that functions with a background electrode in which the background electrode has no GOx sensor (e.g., as discussed below in relation to FIGS. 8 and 9). The system may then compare the first signal and the second signal to detect ingestion of a medication by the user. The system may generate a sensor glucose value based on the comparison. In the embodiment illustrated in FIG. 6, an op amp 630 or other servo-controlled device may connect to sensor electrodes 610 through a circuit/electrode interface 638. The op amp 630, utilizing feedback through the sensor electrodes, attempts to maintain a prescribed voltage (what the DAC may desire the applied voltage to be) between a reference electrode 632 and a working electrode 634 by adjusting the voltage at a counter electrode 636. Current may then flow from a counter electrode 636 to a working electrode 634. Such current may be measured to ascertain the electrochemical reaction between the sensor electrodes 610 and the biomolecule of a sensor that has been placed in the vicinity of the sensor electrodes 610 and used as a catalyzing agent. The circuitry (e.g., processing circuitry) disclosed in FIGS. 7-8 may be utilized in a long-term or implantable sensor or may be utilized in a short-term or subcutaneous sensor.

In a long-term sensor embodiment, where a GOx enzyme is used as a catalytic agent in a sensor, current may flow from the counter electrode 636 to a working electrode 634 only if there is oxygen in the vicinity of the enzyme and the sensor electrodes 610. Illustratively, if the voltage set at the reference electrode 632 is maintained at about 0.5 volts, the amount of current flowing from the counter electrode 636 to a working electrode 634 has a fairly linear relationship with unity slope to the amount of oxygen present in the area surrounding the enzyme and the electrodes. Thus, increased accuracy in determining an amount of oxygen in the blood may be achieved by maintaining the reference electrode 632 at about 0.5 volts and utilizing this region of the current-voltage curve for varying levels of blood oxygen. Different embodiments may utilize different sensors having biomolecules other than a glucose oxidase enzyme and may, therefore, have voltages other than 0.5 volts set at the reference electrode.

As discussed above, during initial implantation or insertion of the sensor 610, the sensor 610 may provide inaccurate readings due to the adjusting of the subject to the sensor and also electrochemical byproducts caused by the catalyst utilized in the sensor. A stabilization period is needed for many sensors in order for the sensor 610 to provide accurate readings of the physiological parameter of the subject. During the stabilization period, the sensor 610 does not provide accurate blood glucose measurements. Users and manufacturers of the sensors may desire to improve the stabilization timeframe for the sensor so that the sensors can be utilized quickly after insertion into the subject's body or a subcutaneous layer of the subject.

In previous sensor electrode systems, the stabilization period or timeframe was one hour to three hours. In order to decrease the stabilization period or timeframe and increase the timeliness of accuracy of the sensor, a sensor (or electrodes of a sensor) may be subjected to a number of pulses rather than the application of one pulse followed by the application of another voltage. for the second time period. In one embodiment, the first voltage may be 1.07 volts. In an embodiment, the first voltage may be 0.535 volts. In an embodiment, the first voltage may be approximately 0.7 volts.

Figure 7:
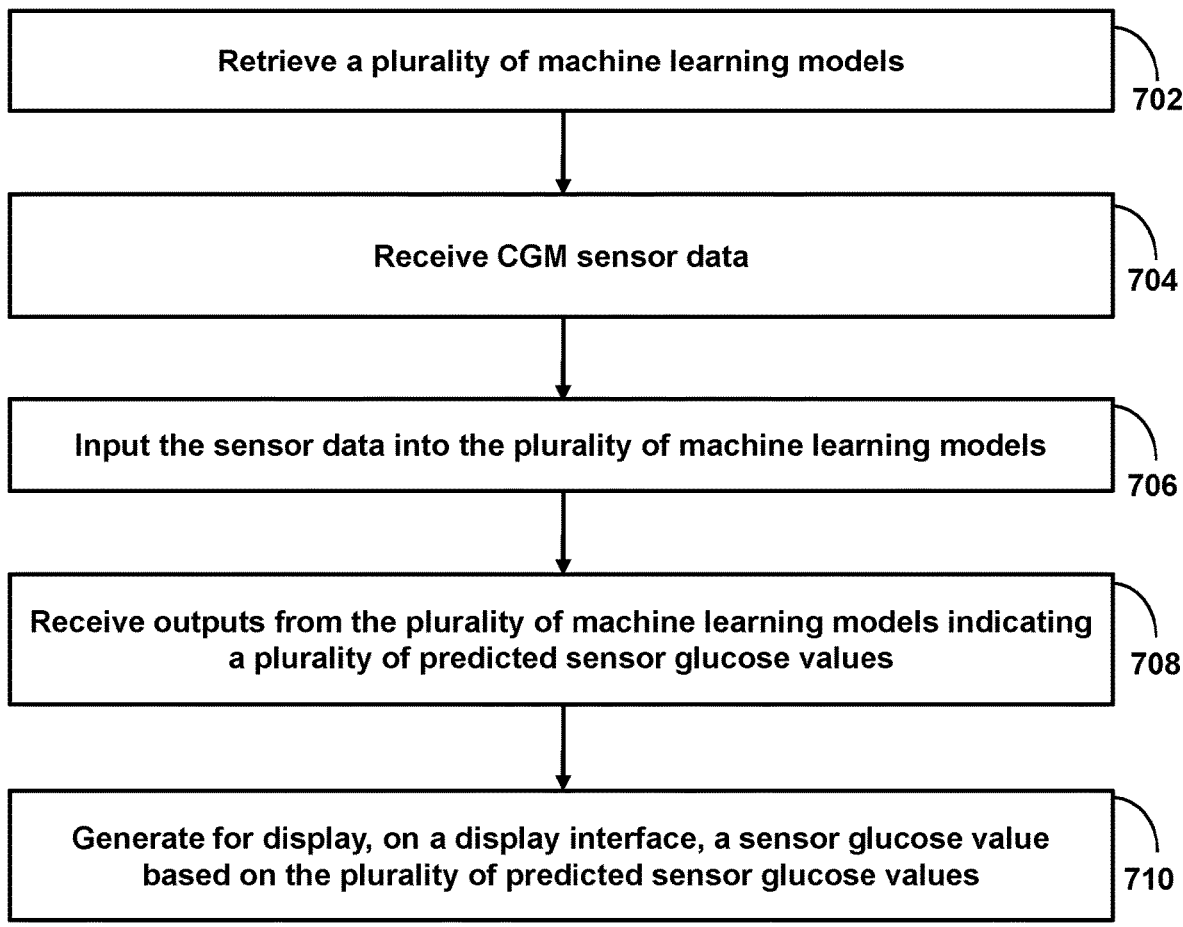
FIG. 7 shows a flowchart of the steps involved in applying layered prediction models to reduce sensor glucose signal blanking, in accordance with one or more embodiments.

FIG. 7 shows a flowchart of the steps involved in applying layered prediction models (e.g., supervised machine learning models, unsupervised machine learning models, semi-supervised machine learning models, or any other suitable type of machine learning models) to reduce sensor glucose signal blanking, in accordance with one or more embodiments. For example, process 700 may represent the steps taken by one or more devices as shown in FIGS. 1-6.

At step 702, process 700 (e.g., using components described in FIGS. 1-6) retrieves a plurality of machine learning models. In some embodiments, the machine learning models may be trained to predict sensor glucose values. In some embodiments, each machine learning model may differ from one another with respect to one or more data characteristics. For example, data characteristics may include sensor data availability, sensor data accuracy, or probabilistic reliance. For example, process 700 may retrieve a first machine learning model that is able to predict sensor glucose values based on available and accurate sensor data (e.g., normal conditions). Process 700 may retrieve a second machine learning model that is able to predict sensor glucose values based largely on sensor data and partially on probabilistic information (e.g., under conditions in which some accurate sensor data is lacking). For example, process 700 may detect a brief abnormality in the sensor data (e.g., a spike) and may therefore remove or minimize the impact of the abnormal sensor data in the final output calculation, relying more on the remaining reliable sensor data as well as probabilistic information. Process 700 may retrieve a third machine learning model that is able to predict sensor glucose values based largely on probabilistic information and partially on sensor data (e.g., under conditions in which accurate sensor data is extremely lacking). For example, process 700 may detect a long-term abnormality in the sensor data (e.g., sensitivity loss) and may therefore disregard or minimize the impact of a large portion of the sensor data in the final output calculation. Process 700 may instead rely heavily on probabilistic data to predict a sensor glucose value. In some embodiments, probabilistic reliance may be based on past sensor data trends from one or more users.

At step 704, process 700 (e.g., using components described in FIGS. 1-6) receives CGM sensor data. For example, process 800 may receive the sensor data at a sensor device. For example, the sensor data may comprise an Interstitial Current Signal ("Isig"), Electrochemical Impedance Spectroscopy Signal ("EIS"), and counter voltage ("Vcntr").

At step 706, process 700 (e.g., using components described in FIGS. 1-6) inputs the sensor data into the plurality of machine learning models. At step 708, process 700 (e.g., using components described in FIGS. 1-6) receives an output from the plurality of machine learning models indicating a plurality of predicted sensor glucose values.

At step 710, process 700 (e.g., using components described in FIGS. 1-6) generates for display, on a display interface, a sensor glucose value based on the plurality of predicted sensor glucose values. For example, in some embodiments, process 700 may identify machine learning models of the plurality of machine learning models which generate results or output results that are compliant with iCGM criteria. In some embodiments, process 700 may rank these machine learning models according to their probabilistic reliance. Process 700 may then select a sensor glucose value from the plurality of predicted sensor glucose values that is associated with a machine learning model having a lowest probabilistic reliance. In some embodiments, process 700 may select a specific model from the trained machine learning models that is appropriate for the sensor data conditions. For example, process 700 may select the machine learning model based on an amount of reliable data (e.g., without abnormalities). If the sensor data is accurate and reliable, process 700 may select a machine learning model that relies solely on the sensor data. If the sensor data is mostly accurate and reliable, process 700 may select a machine learning model that relies heavily on the sensor data and partially on probabilistic information. If the sensor data is unreliable, process 700 may select a machine learning model that relies mostly on probabilistic information and only partially on the sensor data, and so on. In some embodiments, the sensor glucose value may be based on a weighted average of the plurality of predicted sensor glucose values. In some embodiments, process 700 may select a specific model based on past positive user experience with that model during a specific time period that includes time of day and day of the week or activity state, such as exercise or meals. In these embodiments, process 700 may rely on information generated from one or more users regarding the performance of various models during one or more time periods or activity states.

It is contemplated that the steps or descriptions of FIG. 7 may be used with any other embodiment of this disclosure. In addition, the steps and descriptions described in relation to FIG. 7 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-5 could be used to perform one or more of the steps in FIG. 7.

Figure 8:
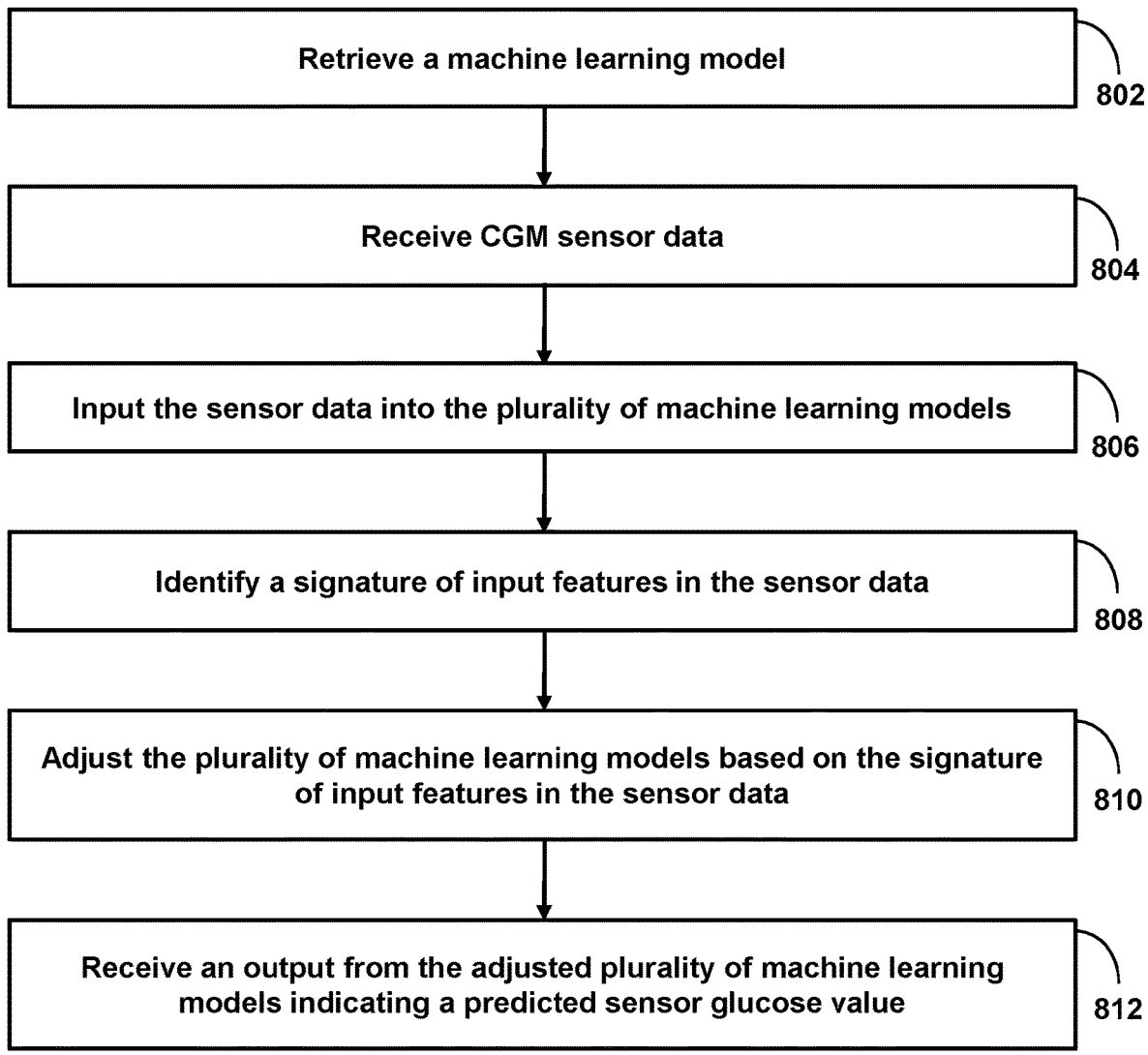
FIG. 8 shows a flowchart of the steps involved in applying micro models to estimate sensor glucose values under outlier conditions, in accordance with one or more embodiments.

FIG. 8 shows a flowchart of the steps involved in applying micro models (e.g., supervised machine learning models, unsupervised machine learning models, semi-supervised machine learning models, or any other suitable type of machine learning models) to estimate sensor glucose values under outlier conditions, in accordance with one or more embodiments. For example, process 800 may represent the steps taken by one or more devices as shown in FIGS. 1-6.

At step 802, process 800 (e.g., using components described in FIGS. 1-6) retrieves a plurality of machine learning models (e.g., micro models). In some embodiments, the machine learning models may be trained to predict sensor glucose values. In some embodiments, each machine learning model may predict sensor glucose values under a particular condition. In some embodiments, each particular condition may be a condition or scenario that differs from standard conditions (e.g., an outlier condition). For example, outlier conditions may include types of users of a sensor device (e.g., young users, physically active users, users with high glucose levels, users whose glucose variation is higher than the population average, etc.). In some embodiments, outlier conditions may include environmental conditions (e.g., high elevation, high environmental temperature, etc.). In some embodiments, outlier conditions may include wear conditions (e.g., high levels of wear due to the sensor experiencing use over a long period of time, location of wear on the body, etc.). In some embodiments, outlier conditions may include manufacturing or fabrication conditions (e.g., glucose limiting membranes may differ slightly between sensor devices due to manufacturing variations, leading to differences in sensitivity across sensor devices, equipment brought in as replacement on the production line may perform slightly differently from the equipment it is replacing on the line, etc.). In some embodiments, outlier conditions may include user activity conditions (e.g., running, jumping, etc.). In some embodiments, each machine learning model may be trained using training data which includes clinical data for a particular outlier condition (e.g., as described above). In some embodiments, each machine learning model may be trained using a combination of standard training data and outlier training data. For example, a first machine learning model of the plurality of machine learning models may be trained to predict sensor glucose values for users who are very physically active using clinical data from physically active users along with standard clinical data. In some embodiments, a second machine learning model of the plurality of machine learning models may be trained to predict sensor glucose values for users in high environmental temperatures using clinical data from sensor devices that operated in high environmental temperatures as well as standard clinical data, and so on.

At step 804, process 800 (e.g., using components described in FIGS. 1-6) receives CGM sensor data. For example, process 800 may receive the sensor data at a sensor device. For example, the sensor data may comprise an Interstitial Current Signal ("Isig"), Electrochemical Impedance Spectroscopy Signal ("EIS"), and counter voltage ("Vcntr").

At step 806, process 800 (e.g., using components described in FIGS. 1-6) inputs the sensor data into the plurality of machine learning models. At step 808, process 800 (e.g., using components described in FIGS. 1-6) identifies a signature of input features in the sensor data. In some embodiments, a signature of input features may include characteristics of the sensor data. For example, process 800 may recognize a pattern, trend, or behavior of one or more input features of the sensor data (e.g., sensitivity loss, sensitivity increase, spikes, drop-offs, periodic behaviors, etc.). In some embodiments, process 800 may analyze real-time input features, trending input features, or input features across lifetime sensor data of a sensor device. Process 800 may identify a signature of input features in the sensor data by matching a combination of the input features with sensor data with a predetermined signature of input features in a database. In some embodiments, the signatures of input features in the database may each be associated with a particular outlier condition.

At step 810, process 800 (e.g., using components described in FIGS. 1-6) adjusts the plurality of machine learning models based on the signature of input features in the sensor data. For example, process 800 may identify one or more machine learning models of the plurality of machine learning models that are associated with the identified signature of input features. For example, the one or more machine learning models may be trained to predict sensor glucose values under conditions that match the identified signature of input features. Process 800 may then adjust the plurality of machine learning models to feature or prioritize the one or more machine learning models that are associated with the identified signature of input features. For example, process 800 may select the one or more machine learning models such that the one or more machine learning models operate as the prime model or models. Process 800 may increase weights associated with the one or more machine learning models such that a weighted average of the plurality of machine learning models features the one or more machine learning models associated with the identified signature of input features most prominently. In some embodiments, process 800 may employ these or other methods of featuring or prioritizing the one or more machine learning models associated with the identified signature of input features.

At step 812, process 800 (e.g., using components described in FIGS. 1-6) receives an output from the adjusted plurality of machine learning models indicating a predicted sensor glucose value. In some embodiments, the adjusted plurality of machine learning models may include the one or more machine learning models associated with the identified signature of input features being featured solely or most prominently. In some embodiments, the output from the adjusted plurality of machine learning models may include an average, median, maximum, minimum, or weight of outputs from multiple models (e.g., the one or more machine learning models associated with the identified signature of output features). In some embodiments, process 800 may display the predicted sensor glucose value, on a display interface, of the sensor device based on the output.

It is contemplated that the steps or descriptions of FIG. 8 may be used with any other embodiment of this disclosure. In addition, the steps and descriptions described in relation to FIG. 8 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-5 could be used to perform one or more of the steps in FIG. 8.

Figure 9:
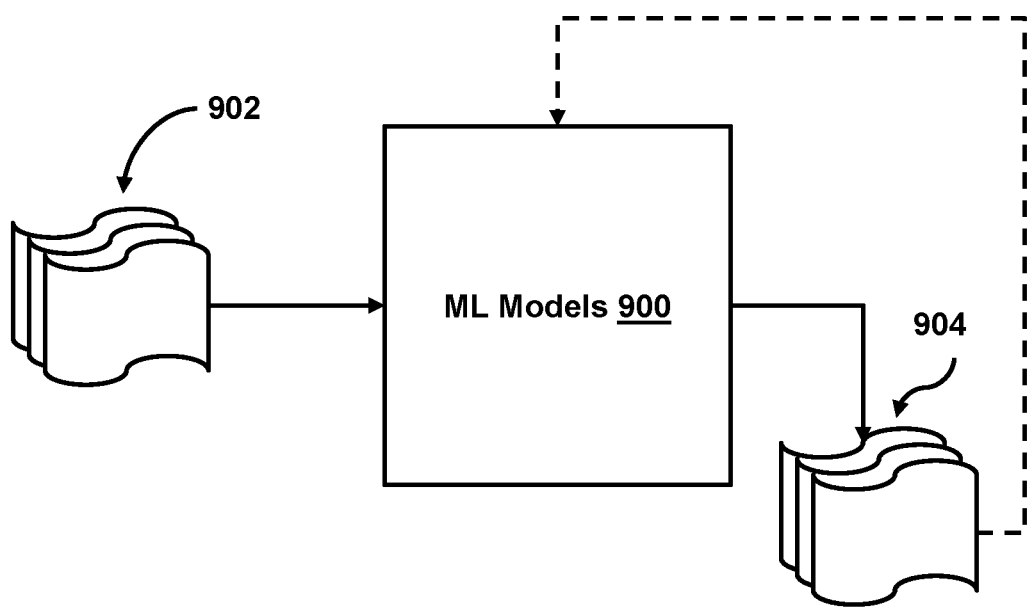
FIG. 9 shows a machine learning model system for making layered predictions that facilitate reduction of sensor glucose signal blanking and predictions that facilitate estimating a sensor glucose value under outlier conditions, in accordance with one or more embodiments.

FIG. 9 shows a machine learning model system for making layered predictions that facilitate reduction of sensor glucose signal blanking and predictions that facilitate estimating a sensor glucose value under outlier conditions, in accordance with one or more embodiments.

In some embodiments, the machine learning model system may include one or more neural networks or other machine learning models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neural unit itself) may have a threshold function such that the signal must surpass the threshold before it propagates to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free flowing, with connections interacting in a more chaotic and complex fashion.

In some embodiments, the machine learning model system may update its configurations (e.g., weights, biases, or other parameters) based on its assessment of the predictions. Memory may store training data and one or more trained machine learning models.

As an example, a machine learning model 900 may take inputs 902 and provide outputs 904. In one use case, outputs 904 may be fed back (e.g., active feedback) to machine learning model 900 as input to train machine learning model 900 (e.g., alone or in conjunction with user indications of the accuracy of outputs 904, labels associated with the inputs 902, or with other reference feedback information). In another use case, machine learning model 900 may update its configurations (e.g., weights, biases, or other parameters) based on its assessment of its prediction (e.g., outputs 904) and reference feedback information (e.g., user indication of accuracy, reference labels, or other information). In another use case, where machine learning model 900 is a neural network, connection weights may be adjusted to reconcile differences between the neural network's prediction and the reference feedback. In a further use case, one or more neurons (or nodes) of the neural network may require that their respective errors be sent backward through the neural network to them to facilitate the update process (e.g., backpropagation of error). Updates to the connection weights may, for example, be reflective of the magnitude of error propagated backward after a forward pass has been completed. In this way, for example, the machine learning model 900 may be trained to generate better predictions.

In some embodiments, methods and systems described herein may include a plurality of machine learning models trained to make predictions that facilitate reduction of sensor glucose signal blanking. In some embodiments, inputs 902 may comprise CGM sensor data (e.g., glucose sensor data) and prior modeling data, and reference feedback information 904 (which is fed back as input to the machine learning model 900) may include clinical data on sensor glucose behavior. For example, the clinical data may be labeled training data (e.g., labeled with trends, behaviors, etc.). Accordingly, when particular sensor data is provided as input 902 to each machine learning model 900, each machine learning model 900 may provide an output 904 including a predicted sensor glucose value.

In some embodiments, each machine learning model 900 may be trained to select certain inputs 902 over others or weigh certain inputs 902 more heavily than others. For example, systems and methods described herein may include N machine learning models. The first machine learning model may rely solely on inputs 902 which comprise CGM sensor data. The reference feedback information 904 may include clinical data on sensor glucose behavior. When particular sensor data is provided as input 902, the first machine learning model may provide an output 904 which indicates a predicted sensor glucose value based solely on the CGM sensor data inputs. A second machine learning model may rely on inputs 902 which include both CGM sensor data and prior modeling information. The reference feedback information 904 may include clinical data on sensor glucose behavior. When particular sensor data is provided as input 902, the second machine learning model may provide an output 904 which indicates a predicted sensor glucose value based on both the CGM sensor data and probabilistic projections (e.g., according to the prior modeling information). The N machine learning models may include machine learning models which rely on a range of such inputs 902 (e.g., based on selections, averages, weighting, etc.).

In some embodiments, methods and systems described herein may include a plurality of machine learning models trained to make predictions that facilitate estimating a sensor glucose value under outlier conditions. For example, in some embodiments, inputs 902 may comprise CGM sensor data, and reference feedback information 904 (which is fed back as input to the machine learning model 900) may include clinical data on outlier conditions. For example, each machine learning model may be trained with clinical data that is specific to an outlier condition (e.g., high physical activity levels, high environmental temperature, high sensor temperatures, high altitude, manufacturing variations, etc.). The clinical data may include data from sensor devices that operated under that particular outlier condition. In some embodiments, the training data for each machine learning model may include standard training data (e.g., clinical data not specific to any outlier condition) in addition to the clinical data on the particular outlier condition. The clinical data may be labeled training data (e.g., labeled according to an outlier condition with which it is associated). When machine learning model 900 receives inputs 902, machine learning model 900 may provide an output 904 including a predicted sensor glucose value.

While machine learning model 900 is described in relation to the foregoing examples, it should be understood that machine learning model 900 may be trained to sensor glucose values according to any other criteria or based on any other inputs. In some embodiments, the outputs from machine learning model 900 may be utilized to determine blanking and termination of signals (e.g., as described below in relation to FIG. 10).

Figure 10:
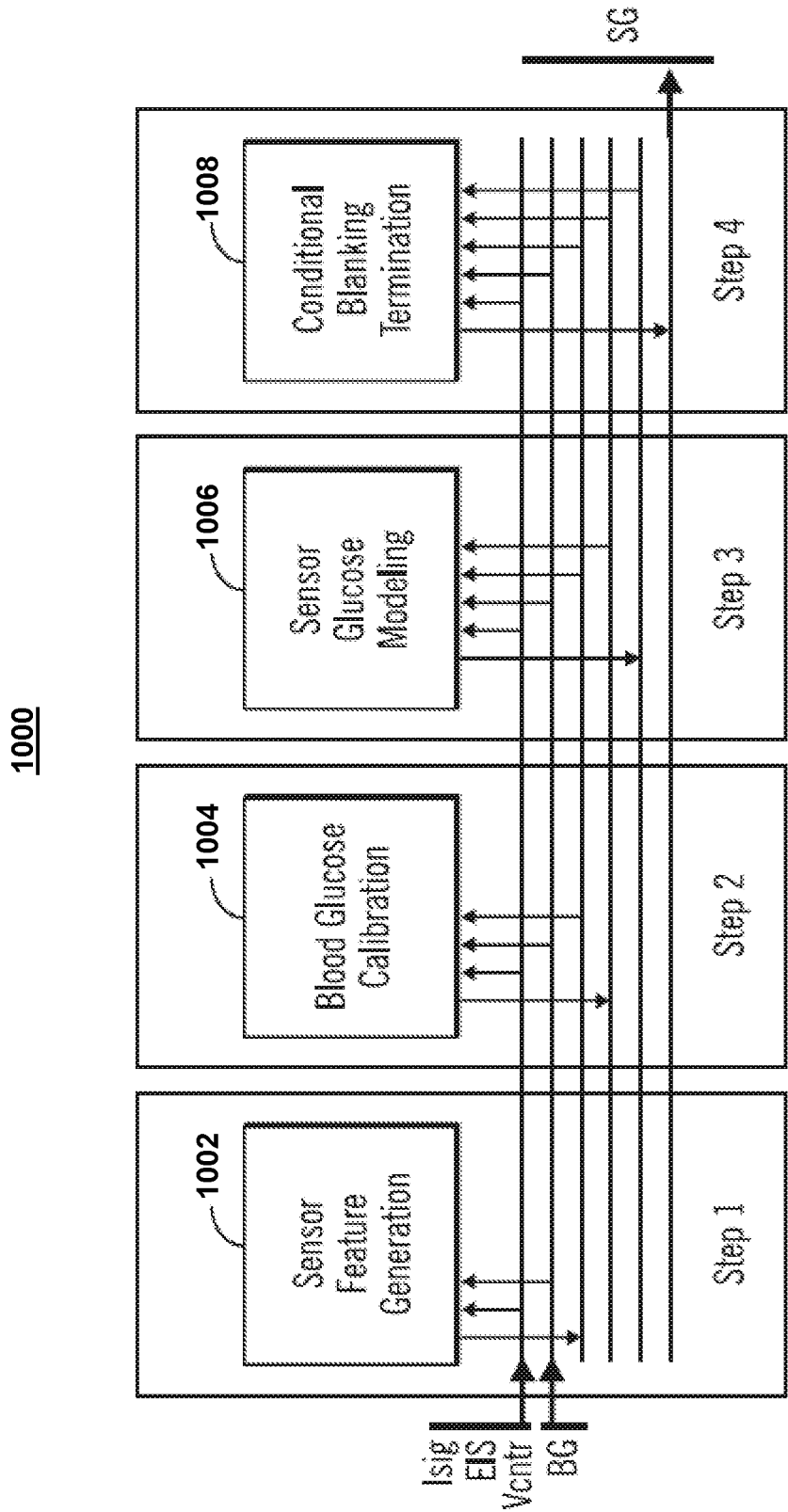
FIG. 10 shows a flow diagram for input data to be transformed to sensor glucose values, in accordance with one or more embodiments.

FIG. 10 shows a flow diagram 1000 for input data to be transformed to sensor glucose values, in accordance with one or more embodiments. As shown schematically in FIG. 10, the methods and systems herein include: a sensor feature generator 1002, a blood glucose calibrator 1004, a sensor glucose modeler 1006, and a conditional blanker and terminator 1008. In some embodiments, the sensor glucose modeler (1002) may receive raw interstitial current signals, electrochemical impedance spectroscopy signals, and counter voltage signals and extracts the input features used by downstream machine learning models. The blood glucose calibrator (1004) may be responsible for receiving input blood glucose values and adjusting the input sensor features from 1002 accordingly. The sensor glucose modeler (1006) may be responsible for applying machine learning techniques to convert the input signals into sensor glucose values. The conditional blanker and terminator (1008) may apply various logic to determine when to stop displaying sensor output signals or terminate the sensor to reduce the probability of displaying noisy or erroneous information to the user or receiving output device. In some embodiments, terminating the sensor may comprise ceasing transmission of sensor data from the sensor device. In some embodiments, input data (i.e., interstitially measured current (Isig), counter voltage (Vcntr), electrochemical impedance spectroscopy (EIS), and blood glucose calibration values (BG)) may pass through the algorithm to be transformed to sensor glucose values, or SG. The Table below shows the information input and output from each of the four components.

Description of the Information Transfer

| Information Content | Component 1002 | Component 1004 | Component 1006 | Component 1008 |
|---|---|---|---|---|
| Input signals, Isig, Vcntr, EIS, BG | Input | N/A | N/A | Input |
| Base and Derivative Sensor Features Requiring No Calibration | Output | Input | 9Input | Input |
| Base and Derivative Sensor Features Requiring BG Calibration | N/A | Output | Input | Input |
| Initial Estimates of Sensor Glucose Values | N/A | N/A | Output | Input |
| Final Estimates of Sensor Glucose Values | N/A | N/A | N/A | Output |

Systems and methods described herein may improve upon sensor glucose modeler 1006. For example, sensor glucose modeler 1006 may include a number (e.g., N) of machine learning models (e.g., machine learning model 900, as shown in FIG. 9). The N machine learning models may each rely on different input data or may weight input data differently, as described above. As such, some models may make more probabilistic predictions than other models when generating sensor glucose value predictions. Conditional blanker and terminator 1008 may rely on the outputs from each of the N machine learning models when determining whether to blank or terminate the signal. In some embodiments, certain outputs from certain machine learning models may be non-compliant (e.g., based on iCGM criteria) and would therefore require blanking. However, other outputs from different machine learning models may be compliant (e.g., based on iCGM criteria). The system may therefore output a sensor glucose value to a user that is based on one or more compliant machine learning models and may reduce the frequency of signal blanking by conditional blanker and terminator 1008.

Figure 11:
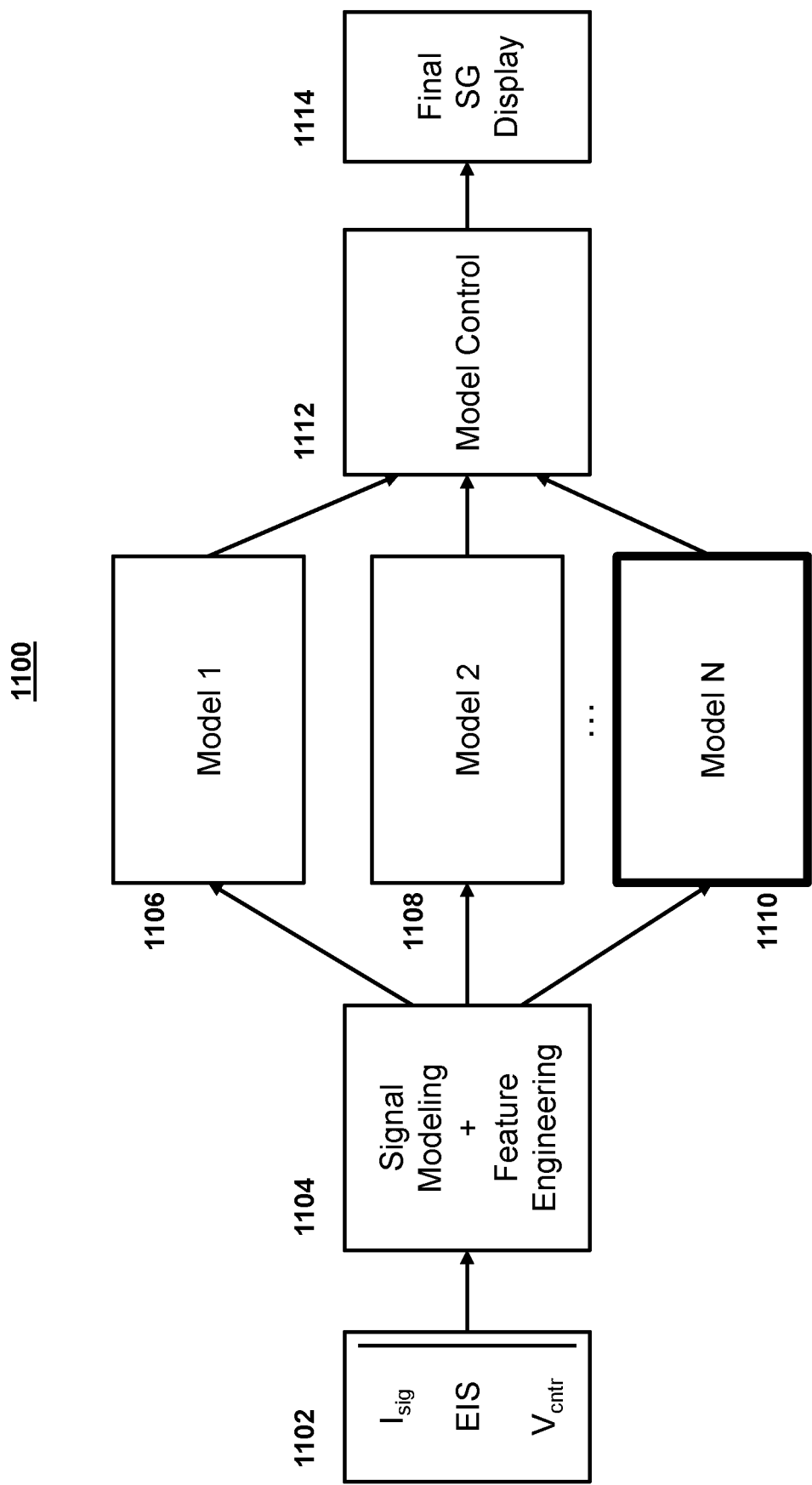
FIG. 11 illustrates a schematic of a sensor glucose modeler of FIG. 10, in accordance with one or more embodiments.

FIG. 11 illustrates shows a schematic 1100 of a sensor glucose modeler 1006 of FIG. 10, in accordance with one or more embodiments. As shown in FIG. 11, inputs 1102 may include Isig, EIS, Vcntr, or other input signals. In some embodiments, inputs 1102 may additionally include prior modeling (e.g., trending) information. Signal modeler and feature engineer 1104 may include N models. For example, models 1106, 1108, and 1110 may include machine learning models which are trained for various inputs or scenarios. As described above in relation to FIG. 9, the machine learning models may be trained to select certain inputs over others or weight certain inputs more heavily than others. For example, model 1 (e.g., 1106) may rely solely on CGM sensor data while model 2 (e.g., 1108) may rely on both CGM sensor data and prior modeling information. The N machine learning models may include machine learning models which rely on a range of such inputs in order to provide more or less probabilistic outputs.

Model controller 1112 may perform selections, averaging, ranking, weighting, or other processing of sensor glucose values, as output by models 1106, 1108, and 1110. For example, model controller 1112 may select a model (e.g., from models 1106, 1108, and 1110) that is the least probabilistic based on a determination that accurate sensor data is readily available. In some embodiments, model controller 1112 may select a model (e.g., from a subset of models 1106, 1108, and 1110 which are compliant with iCGM criteria) that is the least probabilistic. In some embodiments, model controller 1112 may select a model based on other criteria. In some embodiments, model controller 1112 may average the outputs of models 1106, 1108, and 1110 to generate a final sensor glucose value. In some embodiments, model controller 1112 may average the outputs of a subset of models 1106, 1108, and 1110 that are compliant with iCGM criteria in order to generate a final sensor glucose value. In some embodiments, model controller 1112 may average another subset of models 1106, 1108, and 1110. In some embodiments, model controller 1112 may rank models 1106, 1108, and 1110 (e.g., according to how probabilistic, compliant, etc. each model is). In some embodiments, model controller 1112 may rank models 1106, 1108, and 1110 according to other criteria. In some embodiments, model controller 1112 may weight the outputs from models 1106, 1108, and 1110. For example, model controller 1112 may weight outputs which are compliant with iCGM criteria more heavily than those that are not. In some embodiments, model controller 1112 may weight outputs which are less probabilistic more heavily than those that are not (e.g., based on a determination that accurate sensor data is readily available). In some embodiments, model controller 1112 may weight models 1106, 1108, and 1110 or outputs from models 1106, 1108, and 1110 according to these or any other criteria.

In some embodiments, once model controller 1112 has processed the outputs from models 1106, 1108, and 1110, the system may provide a final SG display 1114 to the user. For example, the final SG display 1114 may include a sensor glucose value that is based on the outputs from models 1106, 1108, and 1110, as described above. In some embodiments, the final SG display 1114 may include a confidence score indicating a measure of confidence that the displayed sensor glucose value is correct. In some embodiments, model controller 1112 may adjust the model outputs to favor one or more models associated with the highest levels of confidence.

In some embodiments, model controller 1112 may assess the quality of the sensor glucose value output. Model controller 1112 may receive feedback (e.g., from the user) indicating a level of accuracy of certain sensor glucose value outputs. Model controller 1112 may use this feedback information to favor or disfavor certain models in the future. In some embodiments, model controller 1112 may assess the quality of the sensor glucose value output within the framework of the overall wear of the user or multiple users. For example, model controller 1112 may assess which models are chosen at higher rates than others (e.g., for the user or for multiple users) over the lifetime of a sensor device. This information may lead model controller 1112 to favor the more popular models in the future.

Returning to FIG. 10, Methods and systems described herein improve upon sensor glucose modeler 1006. For example, instead of predicting sensor glucose values using a single model, methods and systems described herein utilize a plurality of micro models, each of which is trained to operate under a particular outlier condition (e.g., young users, physically active users, users with high glucose levels, high elevation, high environmental temperature, high sensor temperature, high levels of wear by the user, atypical location of wear on the body, manufacturing or fabrication variations, etc.). Upon detecting a particular outlier condition based on input features of sensor data, the system may prioritize certain models (of the plurality of micro models) that are trained for the particular outlier condition. This improvement to sensor glucose modeler 1006 is described in further detail in relation to FIG. 12.

In some embodiments, sensor glucose modeler 1006 may distinguish between outlier conditions and error conditions. For example, the system may identify signatures of input features associated with outlier conditions across clinical data. The system may retrospectively match the signatures of input features with outlier conditions that were present in the clinical data. For example, clinical data for sensor devices used at high environmental temperatures may exhibit certain characteristics. The system may store these trends as signatures in a database such that the system may train models to operate under the outlier conditions in the future. In contrast, error conditions may not exhibit such trends across the clinical data. For example, each error condition may affect the sensor data in unique ways that the system cannot classify into an outlier condition. In another example, error conditions may affect the sensor data once, while outlier conditions may affect the sensor data periodically (e.g., every time a user participates in intense physical activity). In some embodiments, conditional blanker and terminator 1008 may blank the sensor data in response to identifying an error condition. Methods and systems described herein improve the system's ability to handle outlier conditions, as described in further detail below.

Figure 12:
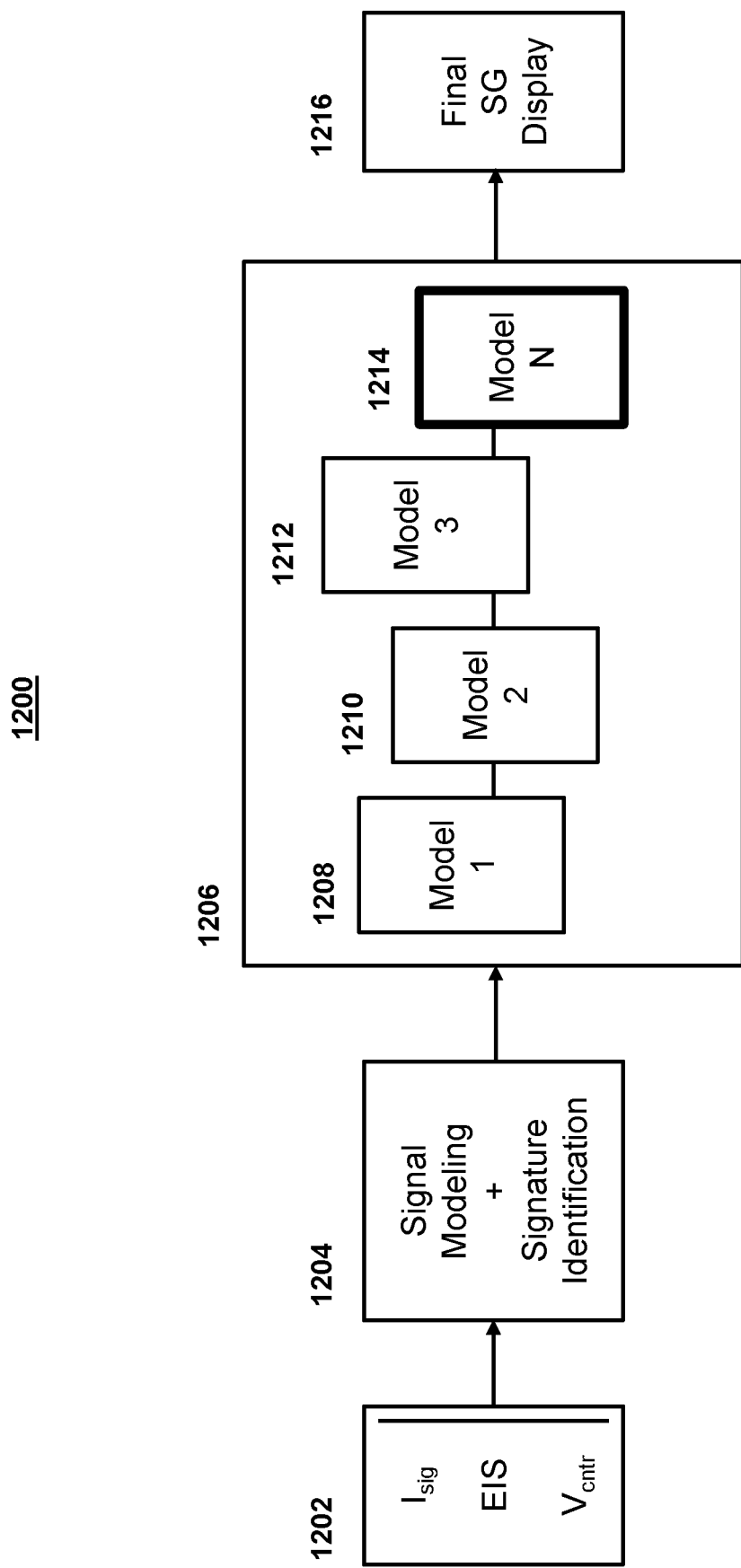
FIG. 12 illustrates a schematic of a sensor glucose modeler of FIG. 10, in accordance with one or more embodiments.

FIG. 12 illustrates a schematic of a sensor glucose modeler of FIG. 10, in accordance with one or more embodiments. As shown in FIG. 12, inputs 1202 may include Isig, EIS, Vcntr, or other input signals. Schematic 1200 may use inputs 1202 for signal modeling and signature identification 1204. For example, signal modeling and signature identification 1204 may model inputs 1202 and identify signatures of the input features of inputs 1202 (e.g., by matching with signatures in a database or other means). In some embodiments, signal modeling and signature identification 1204 may include a plurality of machine learning models 1206. For example, the plurality of machine learning models 1206 may include all models (e.g., models 1-N) that are included in a system. In some embodiments, each model may be trained to operate under a particular outlier condition (e.g., young user, physically active user, user with high glucose levels, high elevation, high environmental temperature, high sensor temperatures, high levels of wear by the user, atypical location of wear on the body, manufacturing or fabrication variations, etc.). For example, model 1208 may be trained to operate under conditions in which the user of the sensor device is very physically active. Model 1210 may be trained for conditions in which the user wears the sensor device on an atypical location of the body (e.g., on the leg). Model 1212 may be trained for conditions in which the sensor is worn at high elevations. Model 1214 may be trained for conditions in which a manufacturing variation resulted in an abnormal glucose limiting membrane.

When signal modeling and signature identification 1204 receives inputs 1202, signal modeling and signature identification 1204 may identify a signature of feature inputs of inputs 1202. For example, signal modeling and signature identification 1204 may search for a signature (e.g., trend, behavior, or pattern) of inputs 1202 which is associated with an outlier condition. If signal modeling and signature identification 1204 identifies a signature of feature inputs within inputs 1202, signal modeling and signature identification 1204 may adjust the plurality of machine learning models 1206 in order to prioritize certain models (e.g., from models 1-N) which are associated with the identified signature of input features in the sensor data (e.g., inputs 1202). For example, signal modeling and signature identification 1204 may identify a signature of input features which indicates that the sensor is being worn at very high elevations on a user who is somewhat physically active. Signal modeling and signature identification 1204 may therefore adjust plurality of machine learning models 1206 to prioritize model 1208, which is trained for physically active users, and model 1212, which is trained for high elevations. For example, signal modeling and signature identification 1204 may increase the weights associated with model 1208 and model 1212. In some embodiments, if signal modeling and signature identification 1204 does not identify signatures associated with model 1210 or model 1214 based on input features of the sensor data, signal modeling and signature identification 1204 may leave model 1210 and model 1214 as they are or may further adjust the plurality of machine learning models 1206 to remove or deemphasize model 1210 or model 1214 (e.g., by decreasing weights associated with model 1210 and model 1214). In some embodiments, signal modeling and signature identification 1204 may select certain models that are associated with signatures identified in the sensor data (e.g., inputs 1202) to operate as the sole models (e.g., excluding model 1210 and model 1214). In some embodiments, signal modeling and signature identification 1204 may utilize other methods of prioritizing models (e.g., model 1208 and model 1212) under particular outlier conditions.

In some embodiments, signal modeling and signature identification 1204 may generate a final sensor glucose display 1216 based on the output or outputs from the plurality of machine learning models 1206. For example, signal modeling and signature identification 1204 may take the average, weighted average, median, maximum, minimum, etc. of the outputs from each of the models 1-N. In some embodiments, signal modeling and signature identification 1204 may take the average, weighted average, median, maximum, etc. of the outputs from each of the models trained for a particular outlier condition (e.g., model 1208 and model 1212). In some embodiments, signal modeling and signature identification 1204 may otherwise process the outputs from models 1-N in order to generate the final SG display 1216.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The present techniques will be better understood with reference to the following enumerated embodiments:

1. A method comprising: receiving, at a sensor device, CGM sensor data; inputting the sensor data into a plurality of machine learning models, wherein each machine learning model of the plurality of machine learning models differs with respect to one or more data characteristics and is trained using training data comprising clinical data on sensor glucose behavior; receiving outputs from the plurality of machine learning models indicating a plurality of predicted sensor glucose values; and generating for display, on a display interface, a sensor glucose value based on the plurality of predicted sensor glucose values.
2. The method of embodiment 1, wherein the one or more data characteristics comprise sensor data availability or sensor data accuracy.
3. The method of any of embodiments 1-2, wherein the one or more data characteristics comprise probabilistic reliance.
4. The method of embodiment 3, wherein the probabilistic reliance is based on past sensor data trends.
5. The method of embodiment 3, further comprising: determining a subset of the plurality of machine learning models for which machine learning models belonging to the subset are compliant with iCGM criteria; ranking the subset of the plurality of machine learning models according to the probabilistic reliance of each machine learning model of the subset; and selecting a sensor glucose value from the plurality of predicted sensor glucose values that is associated with a machine learning model of the subset having a lowest probabilistic reliance.
6. The method of any of embodiments 1-5, wherein the sensor glucose value is based on a weighted average of the plurality of predicted sensor glucose values.
7. The method of any of embodiments 1-6, further comprising generating for display, on the display interface, a confidence value associated with the sensor glucose value.
8. A method comprising: receiving, at a sensor device, CGM sensor data; inputting the sensor data into a plurality of machine learning models, wherein each machine learning model of the plurality of machine learning models is trained to predict a sensor glucose value under a particular outlier condition using training data comprising clinical data on outlier conditions; identifying a signature of input features in the sensor data; adjusting the plurality of machine learning models based on the signature of input features in the sensor data; and receiving an output from the adjusted plurality of machine learning models indicating a predicted sensor glucose value.
9. The method of embodiment 8, further comprising displaying the predicted sensor glucose value, on a display interface, of a sensor device based on the output.
10. The method of any of embodiments 8-9, wherein identifying the signature of input features in the sensor data comprises matching a combination of input features in the sensor data with a predetermined signature of input features in a database.
11. The method of any of embodiments 8-10, wherein adjusting the plurality of machine learning models based on the signature of input features in the sensor data comprises: identify one or more machine learning models of the plurality of machine learning models that are associated with the identified signature of input features; and featuring the one or more machine learning models among the plurality of machine learning models.
12. The method of embodiment 11, wherein featuring the one or more machine learning models among the plurality of machine learning models comprises increasing a weighting associated with the one or more machine learning models.
13. The method of embodiment 11, wherein featuring the one or more machine learning models among the plurality of machine learning models comprises selecting the one or more machine learning models for generating the output.

14. The method of any of embodiments 8-13, wherein the training data for each machine learning model is specific to the particular outlier condition.
15. The method of any of embodiments 8-14, wherein the signature of input features in the sensor data is specific to the particular outlier condition.
16. A tangible, non-transitory, machine-readable medium storing instructions that, when executed by a data processing apparatus, cause the data processing apparatus to perform operations comprising those of any of embodiments 1-15.
17. A system comprising: one or more processors; and memory storing instructions that, when executed by the processors, cause the processors to effectuate operations comprising those of any of embodiments 1-15.
18. A system comprising means for performing any of embodiments 1-15.

What is claimed is:

1. A sensor device for applying micro machine learning models to reduce sensor glucose signal blanking, the sensor device comprising:
   memory configured to store a plurality of machine learning models, wherein each machine learning model of the plurality of machine learning models is trained to predict a sensor glucose value under a particular outlier condition using training data comprising clinical data on the particular outlier condition; and
   a processor configured to:
      receive continuous glucose monitoring (CGM) sensor data;
      identify a signature of input features in the CGM sensor data;
      adjust weights of the plurality of machine learning models based on the signature of input features in the CGM sensor data;
      receive an output from the plurality of machine learning models, the output indicating a predicted sensor glucose value based on weighting outputs of the plurality of machine learning models using the adjusted weights; and
      cause displaying, on a display interface, the output indicating the predicted sensor glucose value such that the sensor glucose signal blanking is reduced.

2. The sensor device of claim 1, wherein identifying the signature of input features in the CGM sensor data comprises matching a combination of input features in the CGM sensor data with a predetermined signature of input features in a database.

3. The sensor device of claim 1, wherein adjusting the weights of the plurality of machine learning models based on the signature of input features in the CGM sensor data comprises: identify one or more machine learning models of the plurality of machine learning models that are associated with the identified signature of input features; and featuring the one or more machine learning models among the plurality of machine learning models.

4. The sensor device of claim 3, wherein featuring the one or more machine learning models among the plurality of machine learning models comprises increasing a weighting associated with the one or more machine learning models.

5. The sensor device of claim 3, wherein featuring the one or more machine learning models among the plurality of machine learning models comprises selecting the one or more machine learning models for generating the output.

6. The sensor device of claim 1, wherein the training data for each machine learning model is specific to the particular outlier condition.

7. The sensor device of claim 1, wherein the signature of input features in the CGM sensor data is specific to the particular outlier condition.

8. A method for applying micro machine learning models to reduce sensor glucose signal blanking, the method comprising:
   receiving, at a sensor device, CGM sensor data;
   inputting the CGM sensor data into a plurality of machine learning models, wherein each machine learning model of the plurality of machine learning models is trained to predict a sensor glucose value under a particular outlier condition using training data comprising clinical data on the particular outlier condition;
   identifying a signature of input features in the CGM sensor data;
   adjusting weights of the plurality of machine learning models based on the signature of input features in the CGM sensor data;
   receiving an output from the plurality of machine learning models, the output indicating a predicted sensor glucose value based on weighting outputs of the plurality of machine learning models using the adjusted weights; and
   causing displaying, on a display interface, the output indicating the predicted sensor glucose value such that the sensor glucose signal blanking is reduced.

9. The method of claim 8, wherein identifying the signature of input features in the CGM sensor data comprises matching a combination of input features in the CGM sensor data with a predetermined signature of input features in a database.

10. The method of claim 8, wherein adjusting the weights of the plurality of machine learning models based on the signature of input features in the CGM sensor data comprises: identify one or more machine learning models of the plurality of machine learning models that are associated with the identified signature of input features; and featuring the one or more machine learning models among the plurality of machine learning models.

11. The method of claim 10, wherein featuring the one or more machine learning models among the plurality of machine learning models comprises increasing a weighting associated with the one or more machine learning models.

12. The method of claim 10, wherein featuring the one or more machine learning models among the plurality of machine learning models comprises selecting the one or more machine learning models for generating the output.

13. The method of claim 8, wherein the training data for each machine learning model is specific to the particular outlier condition.

14. The method of claim 8, wherein the signature of input features in the CGM sensor data is specific to the particular outlier condition.

15. A non-transitory computer-readable medium storing instructions that, when executed by one or more processors, cause operations comprising:
   receiving, at a sensor device, CGM sensor data;
   inputting the CGM sensor data into a plurality of machine learning models, wherein each machine learning model of the plurality of machine learning models is trained to predict a sensor glucose value under a respective, particular outlier condition using training data known to comprise clinical data on the respective, particular outlier condition;

identifying a signature of input features in the CGM sensor data;

adjusting weights of the plurality of machine learning models based on the signature of input features in the CGM sensor data;

receiving an output from the plurality of machine learning models, the output indicating a predicted sensor glucose value based on weighting outputs of the plurality of machine learning models using the adjusted weights; and causing displaying, on a display interface, the output indicating the predicted sensor glucose value such that the sensor glucose signal blanking is reduced.

16. The non-transitory computer-readable medium of claim 15, wherein identifying the signature of input features in the CGM sensor data comprises matching a combination of input features in the CGM sensor data with a predetermined signature of input features in a database.

17. The non-transitory computer-readable medium of claim 15, wherein adjusting the weights of the plurality of machine learning models based on the signature of input features in the CGM sensor data comprises: identify one or more machine learning models of the plurality of machine learning models that are associated with the identified signature of input features; and featuring the one or more machine learning models among the plurality of machine learning models.

18. The sensor device of claim 1, wherein the particular outlier condition includes at least one of:
    an outlier type of user;
    an outlier environmental condition;
    an outlier sensor wearing condition;
    an outlier manufacturing condition; or
    an outlier user activity condition.

* * * * *